United States Patent [19]

Schindler

[11] 4,413,627

[45] Nov. 8, 1983

[54] POLAROGRAPHIC CATHETER PROBE

[75] Inventor: Johannes G. Schindler, Marburg an der Lahn, Fed. Rep. of Germany

[73] Assignee: Dr. E. Fresenius Chemisch-pharmazeutische Industrie KG Apparatebau KG, Bad Homburg, Fed. Rep. of Germany

[21] Appl. No.: 193,599

[22] Filed: Oct. 3, 1980

[30] Foreign Application Priority Data

Oct. 27, 1979 [DE] Fed. Rep. of Germany ....... 2943457

[51] Int. Cl.$^3$ ............................................... A61B 5/00
[52] U.S. Cl. .................................. 128/635; 204/403; 204/406
[58] Field of Search .................... 128/635; 204/195 B, 204/195 P, 195 G

[56] References Cited

U.S. PATENT DOCUMENTS

| | | | |
|---|---|---|---|
| 3,528,403 | 9/1970 | Imredy et al. ........................ | 128/635 |
| 3,605,722 | 9/1971 | Riseman et al. ..................... | 128/635 |
| 3,659,586 | 5/1972 | Johns et al. ......................... | 128/635 |
| 3,930,493 | 1/1976 | Williamson ................. | 204/195 B X |
| 4,016,866 | 4/1977 | Lawton ............................... | 128/635 |
| 4,197,852 | 4/1980 | Schindler et al. .................... | 128/635 |
| 4,252,124 | 2/1981 | Maurer et al. ....................... | 128/635 |

*Primary Examiner*—Lee S. Cohen
*Attorney, Agent, or Firm*—Oblon, Fisher, Spivak, McClelland & Maier

[57] ABSTRACT

A polarographic catheter-shaped probe for determining analytical data of biological fluids of human beings, of animals, or of plants, and having a cathode, an anode and an electrolyte connecting the two, which are surrounded by a flexible sheath sealed in the tip region of the cathode by an ion-impermeable but gas-permeable membrane, wherein the anode is arranged at the distal end of the catheter shaft away from the cathode tip, the electrolyte extends from the anode to the tip of the cathode within the probe, and the anode and cathode are connected to a terminal jack for measuring instruments located at the end of the probe facing the anode. The jack optionally contains a supply chamber for the electrolyte, which is connected in a liquid-tight manner to the one end of the catheter shaft.

13 Claims, 6 Drawing Figures

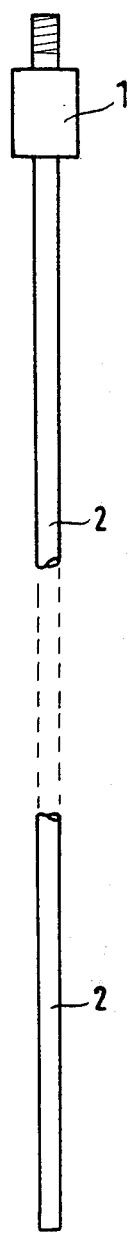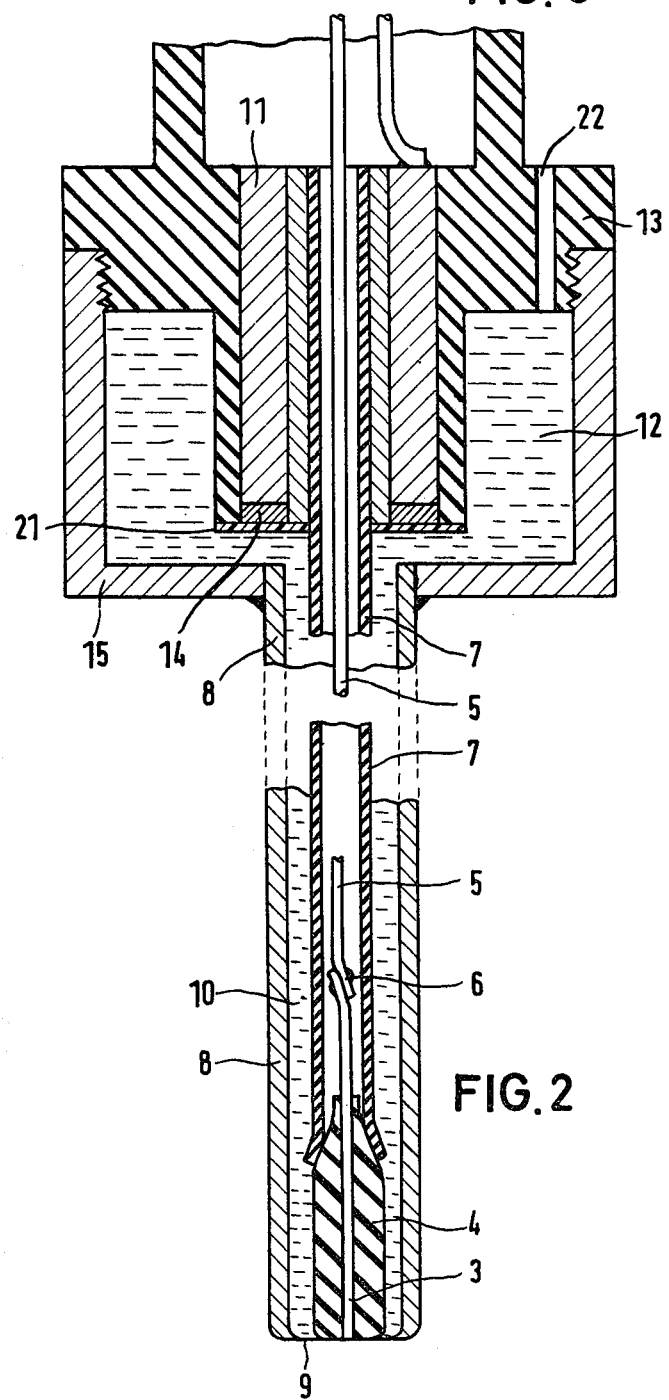

POLAROGRAPHIC CATHETER PROBE

BACKGROUND OF THE INVENTION

1. Field of the Invention

This invention relates to a polarographic catheter-shaped probe for determining the analytical data of biological fluids of humans, of animals, or of plants, and having a cathode, an anode and an electrolyte connecting the two, which are surrounded by a sheath closed by a flexible membrane impermeable to ions in the region of the cathode tip but permeable to gases.

2. Description of the Prior Art

Already known from U.S. Pat. No. 3,528,403 is a sensing probe in which the cathode and the anode are positioned parallel to each other within a plastic structural member and are surrounded by a plastic sheath having a gas-permeable membrane in the region of the tip of the cathode. The electrolyte connecting the cathode with the anode is located in a cavity in the region of the tip of the plastic sheath. This probe is incorporated into a catheter shaft when measurements are made.

In another known sensing probe, disclosed in U.S. Pat. No. 3,758,398, the cathode is concentrically surrounded by the anode, and both are held inside a unit. A cap supporting a gas permeable membrane is filled with electrolyte and is then screwed onto the unit supporting the electrodes.

In U.S. Pat. No. 3,259,124 is disclosed another prior art probe in catheter form. This probe is constructed for taking measurements in the human body and has the electrode arrangement in the front end of a flexible tube closed by a gas-permeable membrane. The electrode arrangement is formed by two concentrically arranged electrodes insulated with respect to each other and extending to the tip of the probe, their conducting relationship established through an electrolyte also provided in the tip of the probe.

Since for all prior art catheter-shaped probes the anode and the cathode are arranged in the region of the tip of the probe and, accordingly, the reservoir for the electrolyte is also located in this region, extreme miniaturization of the primary element becomes very problematical, making great demands with respect to precision during the manufacturing process. The diameters of previously available catheter probes cannot be reduced below 1.5 mm. But this means that such probes can hardly be used for measurements on particularly small living creatures, because these dimensions are still too great for introduction into the fine channels of body fluids.

SUMMARY OF THE INVENTION

Accordingly, one object of this invention is to provide a novel polarographic catheter probe having a particularly small diameter, and being of such a simple construction that it can also be manufactured comparatively inexpensively.

Another object of this invention is to provide a novel polargraphic catheter of decreased diameter which is accordingly simpler to use and correspondingly entails fewer risks during use.

These and other objects are achieved pursuant to the invention by arranging the anode at the distal end of the catheter shaft away from the cathode tip, having the electrolyte extend within the probe from the anode to the cathode tip, and by connecting the anode and cathode to a terminal jack for measuring instruments arranged at the end of the probe facing the anode, wherein the jack optionally contains a supply chamber for the electrolyte and is connected in a liquid-tight manner to the one end of the catheter shaft.

Due to the special separation of anode and cathode, the wiring within the probe is reduced to that of the cathode. This makes it possible for the inner diameter of the probe sheath to be only slightly greater than the diameter of the cathode, because already a thin film of electrolyte liquid is sufficient for the necessary connection of the anode to the cathode in order to conduct polarographic measurements. But this also permits the total diameter of the probe to be kept extremely small. Thus, it is now possible to achieve catheter diameters of 0.8 mm and still smaller.

Further in accordance with the invention, the terminal jack for the electrical connections of the anode and cathode on the one hand and the measuring instruments on the other hand, is located at the end of the probe facing the anode, i.e. at that end which is not introduced into the channel of the liquid that is to be measured. Accordingly, its dimensions need not be miniaturized so that its construction makes no special manufacturing demands, and it can be constructed as sturdy as required. If this terminal jack contains a supply chamber for the electrolyte, then it is connected to the one end of the probe sheath so as to be impervious to liquids. This has the advantage that in comparison with the prior art probes, a relatively large total volume of electrolyte liquid is available, which has a favorable effect on the life of the probe. In addition, it is advantageous to incorporate a barrier layer between the anode and cathode to prevent migration of silver ions from the anode to the cathode.

It is advantageous to have the electrolyte concentrically surround the insulated cathode and extend as an electrolyte column from the electrolyte reservoir provided in the terminal jack up to the cathode tip free of insulating material. The particular advantage of this construction resides in having the electrolyte concentrically surrounding the cathode simultaneously serve as shield of the cathode lead against stray electrical interferences. Experiments have demonstrated that the screening achieved meets all practical requirements and is in no way inferior in its usefulness in comparison to a metal shield.

In accordance with an additional advantageous embodiment, the connection between the electrolyte reservoir and the cathode tip is made with the aid of a fiber strand soaked with electrolyte, or of a capillary system. The one or the other have the property of continuously maintaining an electrolyte bridge between cathode and anode due to capillary action, while the sheath of the probe can tightly surround the cathode and the fiber strand, or the capillary system. Its inner diameter can thus practically be reduced to the diameter of the cathode lead.

The fiber strand or the capillary system can also be advantageously constructed as a shell concentrically surrounding the cathode. The screen against stray electrical interferences already mentioned, is similarly present also when such fiber strand or capillary system is used.

It is preferred that the electrolyte, i.e. potassium chloride or sodium chloride or something similar, also be embedded in a sponge-like or gel-like composition, i.e. agar-agar, with which the insulated cathode is coated.

Also such construction achieves a reduction of the diameter of the probe while simultaneously keeping construction of the probe simple.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a simplified side view of a catheter probe;

FIG. 2 is a transverse cross-sectional view of a catheter tip;

FIG. 3 is a transverse cross-sectional view of a terminal jack;

DESCRIPTION OF THE PREFERRED EMBODIMENTS

Figure 4:
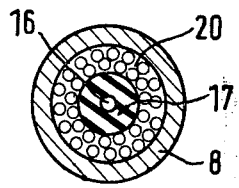
FIG. 4 is a transverse cross-sectional view of a simplified embodiment of the catheter tip.

Referring now to the drawings, wherein like reference numerals designate identical or corresponding parts throughout the several views, and more particularly to FIG. 1 thereof, the catheter probe of the invention includes terminal jack 1 which always remains outside of the body when in use, and the flexible catheter shaft 2 which is inserted into the body, e.g. into a blood vessel. The terminal jack has an electric plug connection for connecting a cable to the measuring apparatus or, in place of the plug, a non-removable electric lead. The length of the catheter shaft 2 can vary between 10 and 50 cm or more, respectively less, depending upon the intended use of the instrument. Its diameter is 0.8 mm or still less.

The most important component of the catheter tip illustrated in FIG. 2 is cathode 3. It consists, e.g., of a platinum wire fused into an insulating jacket 4 of glass. The free end plane of the wire is the actual cathode surface and it has, for example, a diameter of 20 $\mu$m. The wire forming cathode 3 has an electrically conducting connection 6 to the terminal jack also consisting of a wire 5 or of a stranded wire, where said connection ends in the attaching plug or in a non-removable connecting cable. This conducting connection is surrounded by an insulating tube 7. Pursuant to FIG. 4, the parts 3 to 7 mentioned can alternatively also be constructed much simpler, namely in the form of an insulated wire 16 extending from the catheter tip 2 to the terminal jack, whereby wire 16 forms the cathode, as well as also the connecting lead to the terminal jack, and insulating jacket 17 surrounding the same replaces parts 4 and 7 of the arrangement illustrated in FIG. 2. For example, PTFE-insulated (=poly-tetra-fluoroethylene) platinum wires are available that are suitable for this purpose.

The covering of the catheter shaft consists of a tube 8 closed at the lower end by a gas-permeable membrane 9. The inner diameter of this tube is somewhat greater than the outer diameter of the insulating jacket of the cathode, so that in accordance with the invention, an inner space 10 exists filled with liquid electrolyte, e.g. KCl-solution. Membrane 9 is positioned flush to the end plane of the cathode, whereby nevertheless a thin film of liquid is present between cathode and membrane, due to capillary action. To be taken into consideration as membrane material for a polarographic $O_2$-sensor is, for example, PTFE, because of its high permeability to oxygen, and the tube 8 in this instance is suitably also manufactured of PTFE, so that the membrane can be fused to the end of the tube.

The terminal jack illustrated in the transverse view of FIG. 3 contains in accordance with the invention anode 11 and an electrolyte chamber or reservoir 12. In the form illustrated, anode 11 consists of a hollow cylinder fitted sealingly into an insulating part 13 so as to be impervious to liquid. That part of the anode surface exposed to the liquid electrolyte can be provided with a coating 14. Various metals are suitable as anode materials, e.g. silver, whereby in this case coating 14 can consist of silver chloride. The shape of the anode is insignificant as concerns its function and it can be varied depending upon different technical requirements. In the present example, an additional so-called anodic barrier layer 21 is provided, which prevents the silver ions of the anode from passing through.

Figure 5:
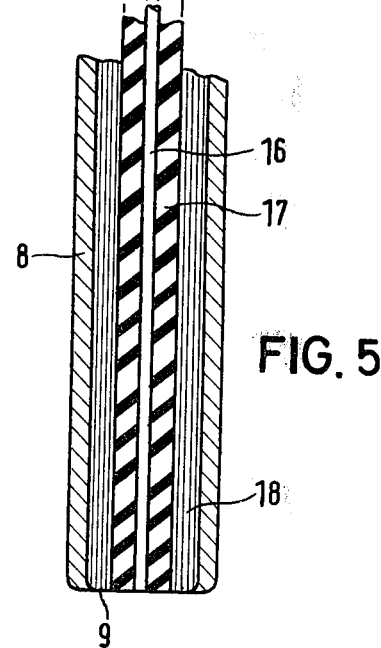
FIG. 5 is a transverse cross-sectional view of a further embodiment of a catheter probe.

Prior to operation of the catheter probe, it is expedient to fill tube 8 and the electrolyte chamber 12 with electrolyte avoiding residual air bubbles. Tube 8 is connected via a liquid-tight seal to a top-cap 15 representing the outer boundary of the electrolyte chamber 12. Top-cap 15 is screwed onto insulating part 13 by means of a thread, whereby the electrolyte thus displaced exits through an overflow aperture 22. This overflow aperture 22 furthermore has the important task of making it possible for the water vapor evaporating through membrane 9 to be replaced by supply-feeding of electrolyte liquid to the catheter tip from the electrolyte chamber 12, thereby maintaining the electrically conducting contact between anode and cathode. Once this attachment is undone, top-cap 15 can again be pulled off together with tube 8 and the electrolyte solution refilled. Thereupon the catheter must be put together again. The liquid column connecting the electrolyte 10 present in supply chamber 12 with the cathode tip pursuant to FIG. 4, has been replaced in the embodiment of the tip of a probe; illustrated in FIG. 5 by a fiber tube 18 or a capillary system 20 surrounding the insulated cathode 16, and also reaching from the supply chamber 12 up to the tip of the probe.

Figure 6:
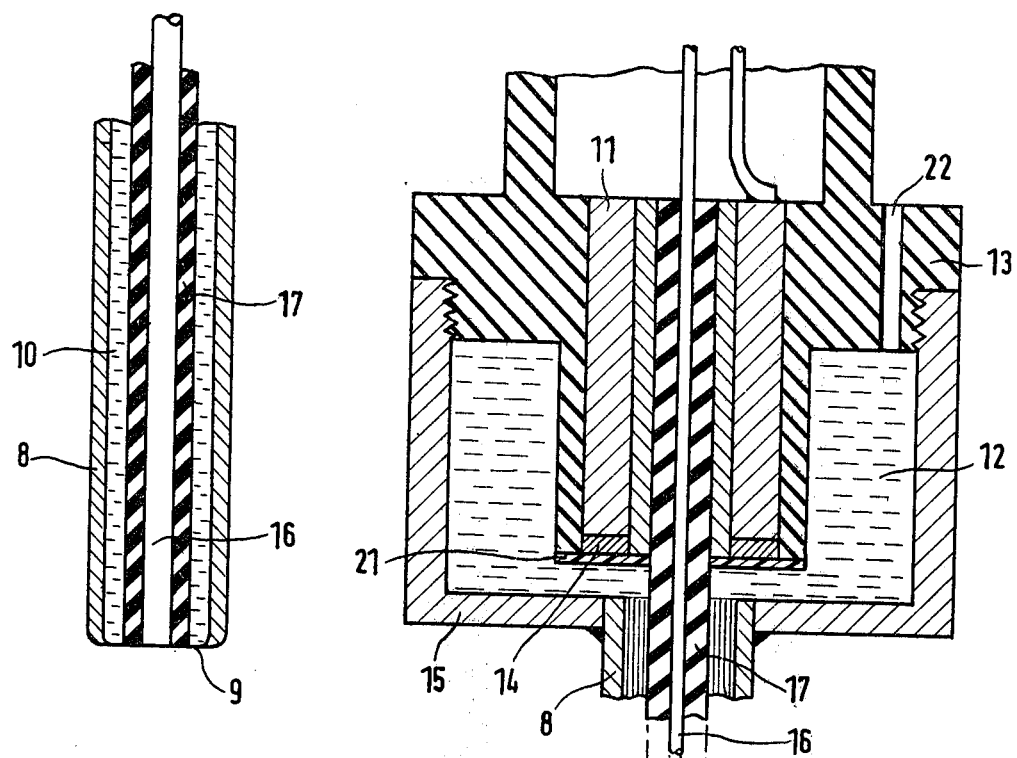
FIG. 6 is a planar cross-sectional view of a catheter probe.

FIG. 6 shows a cross-section of a Pt-cathode 16 coated with an insulation 17, and surrounded by a capillary system 20.

The fiber tube 18 or the capillary system 20 can be formed of plastic, of glass fibers, of plant fibers, of asbestos, of hair, or tissue, of yarn, or similar items.

During operation of the catheter probe, due to the capillary action, the liquid electrolyte will be sucked up from the electrolyte chamber 12 by the tissue and directed to the tip of the probe from where it reaches the tip of the cathode free of insulating material, also as a result of capillary action. This embodiment of the probe insures that obstructions to the catheter shaft occurring while working with the probe but which are not noticed, e.g. constrictions or kinks, will not result in an interruption of the electrolytic connection between anode and cathode, although precisely for this embodiment the distance between the inside wall surface of tube 8 of the probe and the outer surface of insulated cathode 16, 17 is particularly slight, namely, it can be equal to the thickness of the fiber tube 18 or of the capillary system 20.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A polarographic catheter-shaped probe for intravenously determining data of fluids, comprising:
    a cathode;
    an anode;
    an electrolyte disposed between said anode and said cathode;
    a longitudinally extending flexible catheter sheath having opposed ends, said cathode disposed at one end of said sheath to define a cathode tip, said flexible sheath concentrically surrounding said cathode and said electrolyte and provided with an ion-impermeable but gas-permeable membrane at said cathode tip to seal said electrolyte between said flexible sheath and said cathode, said sheath defining a distal end opposite said cathode tip;
    said anode disposed adjacent said distal end of said catheter sheath with the electrolyte extending from said cathode tip to said distal end between said sheath and said cathode; and
    a terminal jack located adjacent the distal end of said sheath and electrically coupled to said anode and cathode, said jack adapted for connecting said anode and cathode to measuring instruments.

2. A probe according to claim 1 wherein said jack comprises:
    a reservoir chamber containing a supply of said electrolyte, said chamber communicating in a liquid-tight manner with electrolyte in the distal end of said catheter sheath.

3. A probe according to claim 2 further comprising:
    an insulating jacket concentrically surrounding said cathode, said cathode having a free end plane abutting said membrane.

4. A probe according to claim 3, wherein said insulating jacket comprises:
    a glass coating formed concentrically on a portion of said cathode adjacent said membrane, and
    a flexible insulating covering surrounding the remaining portion of said cathode.

5. A probe according to claim 3, further comprising:
    said electrolyte concentrically surrounding the insulated cathode and reaching from the electrolyte reservoir chamber provided in the terminal jack up to the free end plane of said cathode insulating jacket.

6. A probe according to claim 2, further comprising:
    a fiber strand or a capillary system extending between the electrolyte reservoir chamber and the cathode tip for producing an electrolytic connection between the cathode tip and the anode as a result of capillary action.

7. A probe according to claim 8, further comprising:
    said fiber strand or said capillary system concentrically surrounding the cathode.

8. A probe according to claim 3, further comprising:
    said insulating jacket coated with a sponge- or gel-like substance reaching from the anode up to the cathode free end plane, in which substance said electrolyte is embedded.

9. A probe according to claim 8, further comprising:
    agar-agar selected as the gel-like substance, into which a salt is embedded as electrolyte.

10. A probe according to claim 9, wherein said electrolyte salt comprises:
    potassium chloride.

11. A probe according to claim 9 wherein said electrolyte salt comprises:
    sodium chloride.

12. A probe according to claim 1, further comprising:
    an insulating coating concentrically surrounding said cathode.

13. A probe according to claim 12, wherein said insulating coating comprises:
    polytetrafluoroethylene.

* * * * *